United States Patent [19]
Park et al.

[11] Patent Number: 6,127,122
[45] Date of Patent: Oct. 3, 2000

[54] METHOD FOR HIGH-SENSITIVE SILVER STAINING

[75] Inventors: Han-Oh Park; Jae-Jong Kim; Jae-Hyung You, all of Seoul, Rep. of Korea

[73] Assignee: Bioneer Corporation, Choongcheongbuk-do, Rep. of Korea

[21] Appl. No.: 09/101,305

[22] PCT Filed: Dec. 30, 1997

[86] PCT No.: PCT/KR97/00283

§ 371 Date: Jul. 2, 1998

§ 102(e) Date: Jul. 2, 1998

[87] PCT Pub. No.: WO98/29567

PCT Pub. Date: Jul. 9, 1998

[30] Foreign Application Priority Data

Dec. 31, 1996 [KR] Rep. of Korea ............... 96-81299

[51] Int. Cl.$^7$ .................................................. C12Q 1/68
[52] U.S. Cl. ................................................................ 435/6
[58] Field of Search .................................................. 435/6

[56] References Cited

U.S. PATENT DOCUMENTS 5,567,585 10/1996 Caetano-Anolles ....................... 435/6

FOREIGN PATENT DOCUMENTS

| 0 610 615 | 8/1994 | European Pat. Off. . |
| WO 94 09 157 | 4/1994 | WIPO . |

OTHER PUBLICATIONS

Bassam, B. J. and Caetano–Anolles, G., Silver Staining of DNA in Polyacrylamide Gels, 42:181–188 (1993).

Bassam, B. J. et al., Fast and Sensitive Silver Staining of DNA in Polyacrylamide Gels, 196:80–83 (1991).

Beidler, J. L. et al., Ultrasensitive Staining of Nucleic Acids with Silver, 126:374–380 (1982).

Gottlieb, M. and Chavko, M., Silver Staining of Native and Denatured Eucaryotic DNA in Agarose Gels, 165:33–37 (1987).

Merril, C. R. et al., Coloration of Silver–Stained Protein Bands in Polyacrylamide Gels is Caused by Light Scattering from Silver Grains of Characteristic Sizes, 85:453–457 (1988).

Somerville, L. L. and Wang, Kuan., The Ultrasensitive Silver "Protein" Stain Also Detects Nanograms of Nucleic Acids, 102(1):53–58 (1981).

Switzer, III, R. C. et al., A Highly Sensitive Silver Stain for Detecting Proteins and Peptides in Polyacrylamide Gels, 98:231–237 (1979).

Wray, W., et al., Silver Staining of Proteins in Polyacrylamide Gels, 118:197–203 (1981).

*Primary Examiner*—Remy Yucel
*Attorney, Agent, or Firm*—Darby & Darby

[57] ABSTRACT

The present invention provides an improved method for silver staining of DNA which comprises the steps of linking DNA to a polymer which has a high affinity for the DNA and binding of a plenty of silver ions to the DNA-polymer complex. The silver staining method of the present invention can be applied for the detection and sequencing of trace amount of DNA.

6 Claims, 3 Drawing Sheets

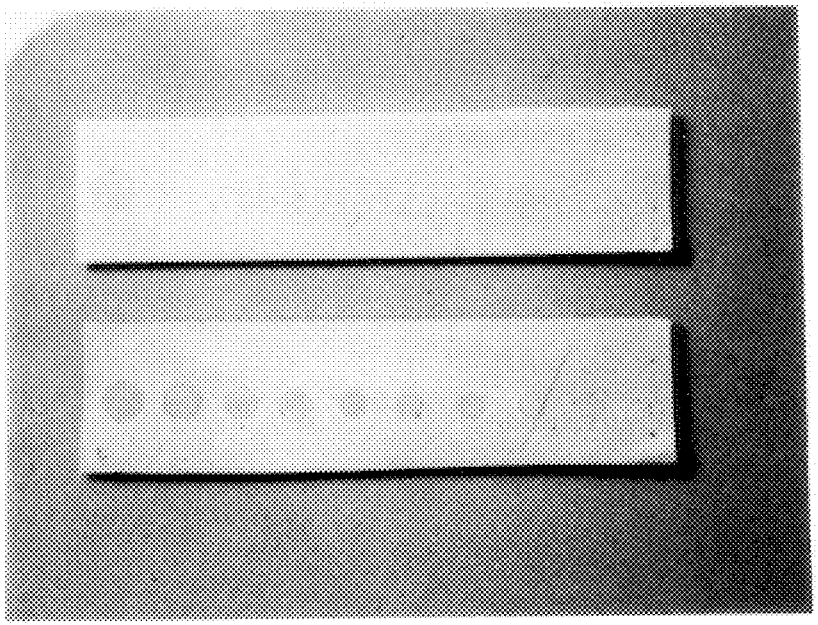
FIG. IA
FIG. IB 1 2 3 4 5 6 7 8 9

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial Sequence
```

-continued

```
<220> FEATURE:
<223> OTHER INFORMATION: Single stranded oligonucleotide primer

<400> SEQUENCE: 1
gttttggctt ccagttccac c                                              21
```

METHOD FOR HIGH-SENSITIVE SILVER STAINING

BACKGROUND OF THE INVENTION

1. Field of the Invention

The present invention relates to a method for high-sensitive silver staining, more specifically, to an improved method for silver staining of DNA which comprises the steps of linking DNA to a polymer which has a high affinity for the DNA and binding of a plenty of silver ions to the DNA-polymer complex.

2. Description of the Prior Art

In general, silver staining is realized by carrying out selective reducing silver ions which are linked to a target material of interest by employing chemical or light (see: Beidler, J. L. et al., Anal. Biochem., 126:374(1982); Goldman. D. and Merril, C. R., Electrophoresis, 3:24(1982)) and detecting light-scattered color of the silver grains produced therefrom (see: Merril, C. R. et al., Proc. Natl. Acad. Sci., USA, 85:453(1988)).

Silver staining methods currently used are largely classified as the following: an alkaline method which reduces a diamine complex of silver nitrate formed under a strong alkaline condition by subjecting the complex in a weakly acidic solution containing formaldehyde; and, an acidic method which reduces silver nitrate in a formaldehyde solution (see: Bassam, B. J. et al., Applied Biochemistry and, Biotechnology, 42:181(1993)).

Although the silver staining technique, at the begining, was developed to detect traces of protein electrophoresed on acrylamide gel (see: Switzer, R. C. et al., Anal. Biochem., 98:231(1979)), through continuous improvement and modification, it has been universally used for detection of lipopolysaccharides (see: Tsai, C. and Frasch, C. E., Anal. Biochem., 119:115(1982)) and nucleic acids (see: Somerville, L. L. and Wang, K., Biochem. Biophys. Res. Commun., 102:54(1981), and proteins as well.

Until now, a variety of silver staining methods for the detection of DNA have been developed as the following: a diamine complex silver staining method (see: Wary, W. et al., Anal. Biochem., 118:197(1981)); an acidic silver staining method (see: Heukeshoven, J. and Dernick, F., Electrophoresis, 6:103(1985); Gottlieb, M. and Chavco, K., Anal. Biochem., 165:33(1987); Bassam, B. J. et al., Anal. Biochem., 98:231(1979)); a cupric-silver method (see: Switzer, R. C. et al., Anal. Biochem., 98:231(1979)) and the like. These silver staining methods are, however, proven to be less satisfactory in the sense that they cannot detect DNA to the level of ng and are not reliable in a view of accuracy and reproducibility.

Accordingly, there are strong reasons for exploring and developing an improved method for detecting DNA with a high sensitivity.

SUMMARY OF THE INVENTION

In this regard, the present inventors, based on Bassam et al's method for silver staining of DNA (see: Bassam B. J. et al., Anal. Biochem., 196:80(1991)), have developed an improved method for silver staining which can detect DNA with a higher sensitivity and reproducibility, compared to the conventional silver staining methods where silver ion is linked to DNA molecule directly.

A primary object of the present invention is, therefore, to provide an improved method for high-sensitive silver staining of DNA molecules.

BRIEF DESCRIPTION OF THE DRAWINGS

The above and the other objects and features of the present invention will become apparent from the following description given in conjunction with the accompanying drawings, in which:

FIG. 1 (A) is a photograph showing a nitrocellulose membrane in which silver staining is carried out by the conventional Bassam et al's method.

FIG. 1 (B) is a photograph showing a nitrocellulose membrane in which silver staining is carried out by the present invention.

FIGS. 2 (B), 2 (C), 2 (D) and 2 (E) are photographs showing nitrocellulose membranes in which silver staining is carried out by the invention through the treatment of 0.05% (v/v), 0.1% (v/v), 0.2% (v/v) and 0.4% (v/v) polyacrylic acid.

FIG. 3 (B) is a photograph showing an acrylamide gel electrophoresis for nucleotide sequencing in which silver staining is carried out by the invention through the treatment of 0.2% (v/v) polyacrylic acid.

DETAILED DESCRIPTION OF THE INVENTION

Figure 2A:
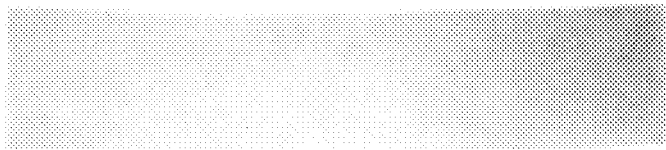
FIG. 2 (A) is a photograph showing a nitrocellulose membrane in which silver staining is carried out by Bassam et al's method.
Figure 2B:
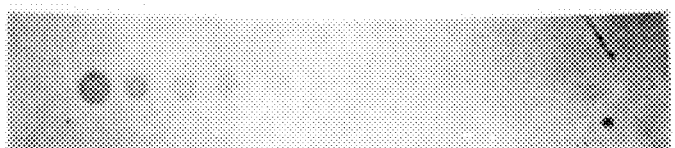
Figure 2C:
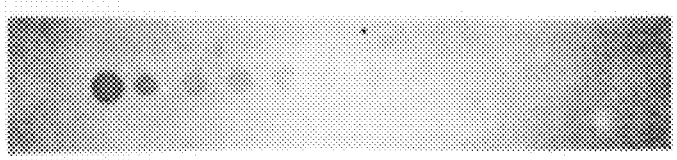
Figure 2D:
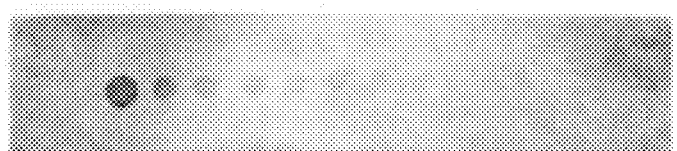
Figure 2E:
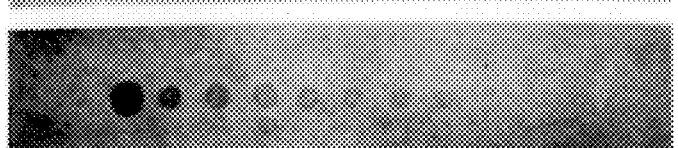

The present inventors have improved the sensitivity of Bassam et al's silver staining method for DNA detection (see: Bassam, B. J. et al., Anal. Biochem., 196:80(1991)) which has been known to be a simple and highly sensitive method, by immersing a gel containing DNA in an aqueous solution containing a polymer and binding silver ions to the DNA-polymer complex. in this regard, the polymer which has a high affinity for DNA molecule, preferably polyacrylic acid or polyethyleneimine, is linked to the DNAs to induce coloring of the silver ions. The concentration of polymer in the aqueous solution (e.g., water), though it may be varied depending on the kind of the polymer, ranges in a concentration of 0.2% (v/v) to 0.4% (v/v), if polyacrylic acid is employed.

In accordance with the silver staining method of the invention, even ng of DNA can be detected with a higher reproducibility, compared to Bassam et al's method which detects $\mu$g of DNA, when DNA is spotted in a round shape of 5 mm in diameter on a nitrocellulose membrane.

The silver staining method of the invention can be applied for nucleotide sequencing and detecting traces of DNA molecules.

The present invention is further illustrated by the following examples, which should not be taken to limit the scope of the invention.

EXAMPLE 1

Effect of Polyacrylic Acid on the Sensitivity of Silver Staining

In order to investigate the effect of polyacrylic acid on the sensitivity of silver staining of DNA, $\lambda$ DNA diluted to a concentration was spotted in a round shape of 5 mm in diameter on a nitrocellulose membrane. After subjecting the membrane in a drying oven maintained at a temperature of 65° C. for 1 hr, it was soaked in 0.2% (v/v) polyacrylic acid solution for 1 min. Then, silver staining was performed in accordance with Bassam et al's method (see: Bassam et al., Anal. Biochem., 196:80(1991)): Silver ion was bound to polyacrylic acid by treating the nitrocellulose membrane with polyacrylic acid and soaking in an aqueous silver containing 1 g/L of silver nitrate solution and 1.5 ml/L formaldehyde for 20 min. The-above nitrocellulose membrane was rinsed with distilled water for 5 sec to eliminate unbound silver ion and subjected in a developing solution containing 30 g/L of sodium carbonate, 3 ml/L of formaldehyde and 2 mg/L of sodium thiosulfate. Then, 7.5% acetic acid was added to stop the reaction when color is sufficiently developed. On the other hand, DNA sample stained with silver nitrate according to Bassam et al's method was used as a control.

FIG. 1(A) shows a nitrocellulose membrane stained with silver nitrate by Bassam et al's method, which has been reported as the best silver staining method so far. FIG. 1(B) shows a nitrocellulose membrane treated with polyacrylic acid by the invented method. In FIGS. 1(A) and 1(B), lanes 1–9 contain 1 μg, 500 ng, 250 ng, 125 ng, 60ng, 40 ng, 2 ng, 1 ng and 100 pg of λ DNA, respectively. As shown in FIGS., 1(A) and 1(B), the invented method which employs polyacrylic acid can detect 1 ng of DNA with a higher sensitivity, compared to the conventional Bassam et al's method which can detect 1 μg of DNA. These results demonstrate that the newly developed silver staining method improves the sensitivity of detection of DNA.

EXAMPLE 2

Effect of Polyacrylic Acid Concentration on the Sensitivity of Silver Staining

In order to investigate the optimal polyacrylic acid concentration, silver staining was performed by using 0.05% (v/v), 0.1% (v/v), 0.2% (v/v) and 0.4% (v/v) polyacrylic acid, respectively, in an analogous manner as in Example 1 (see: FIGS. 2(A)–2(E)). FIG. 2(A) shows a nitrocellulose membrane in which silver staining is carried out by Bassam et al's method and FIGS. 2(B) to 2(E) show nitrocellulose membranes in which silver staining is carried out through the treatment with 0.05% (v/v), 0.1% (v/v), 0.2%(v/v) and 0.4% (v/v) polyacrylic acid, respectively. In FIGS. 2(A) to 2(E), lanes 1–9 contain 1 μg, 500 ng, 250 ng, 125 ng, 60 ng, 40 ng, 12 ng, 1 ng and 100 pg of λ DNA, respectively.

As shown in FIGS. 2(B) to 2(E), the sensitivity increased with the concentration of polyacrylic acid, while background signal also increased at a concentration above 0.4% (v/v). Accordingly, it was determined that the optimal concentration of polyacrylic acid for silver staining is about 0.2% (v/v).

EXAMPLE 3

Silver Staining of DNA Sequencing Gel

In order to investigate the effect of polyacrylic acid on the sensitivity of silver staining in DNA sequencing polyacrylamide gel, DNA sequencing reactions were performed by using 200 ng, 100 ng, 40 ng, 20 ng and 10 ng of template DNA, respectively, which was separated on 6% polyacrylamide gel electrophoresis and stained with silver nitrate.

The DNA sequencing reactions were performed by using Top™ DNA sequencing kit (Bioneer Corporation, Korea) as the following: First, the template DNA (497 base pair PCR product) was mixed with 30 pmoles of primer, SEQ ID NO: (5'GTTTTGGCTTCCAGTTCCACC-3'), and the final volume was adjusted to 40 μl with distilled water. Then, 10 μl aliquots of the samples were added to four separate reaction tubes containing Top™ DNA polymerase, 50 mM Tris-HCl buffer(containing 2 mM $MgCl_2$, pH 8.3) and G(20 μM of ddGTP/6 μM dNTP), A(170 μM of ddATP/6 μM dNTP), T(300 μM of ddTTP/6 μM DNTP) and C(200 μM of ddCTP/6 μM dNTP), respectively. 40 rounds of PCR cycling was carried out as the following: 94° C. for 5 min (predenaturation), 94° C. for 30 sec(denaturaion) 55 ° C. for 30 sec(annealing), and 72° C. for 1 min(extension). At the end of the amplification reaction, 4 μl of stop solution containing 98% formamide, 10 mM EDTA, 0.025% xylene cyanol and 0.025% bromophenol blue was added to each reaction tube. After heating for 5 min at 95° C., each reaction was analyzed on a 6% polyacrylamide gel.

Figure 3A:
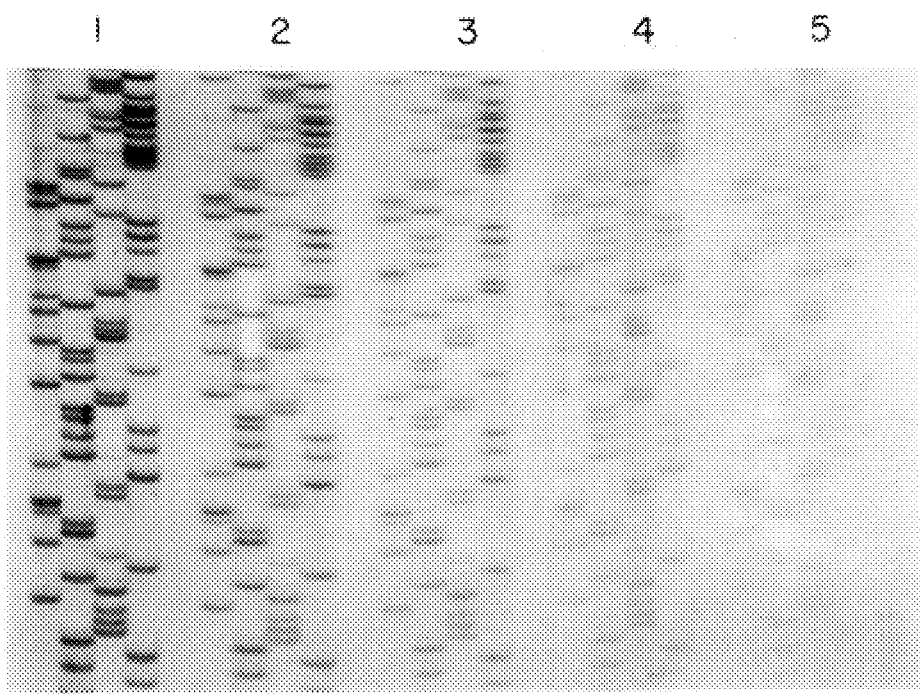
FIG. 3 (A) is a photograph showing an acrylamide gel electrophoresis for nucleotide sequencing in which silver staining is carried out by Bassam et al's method.
Figure 3B:
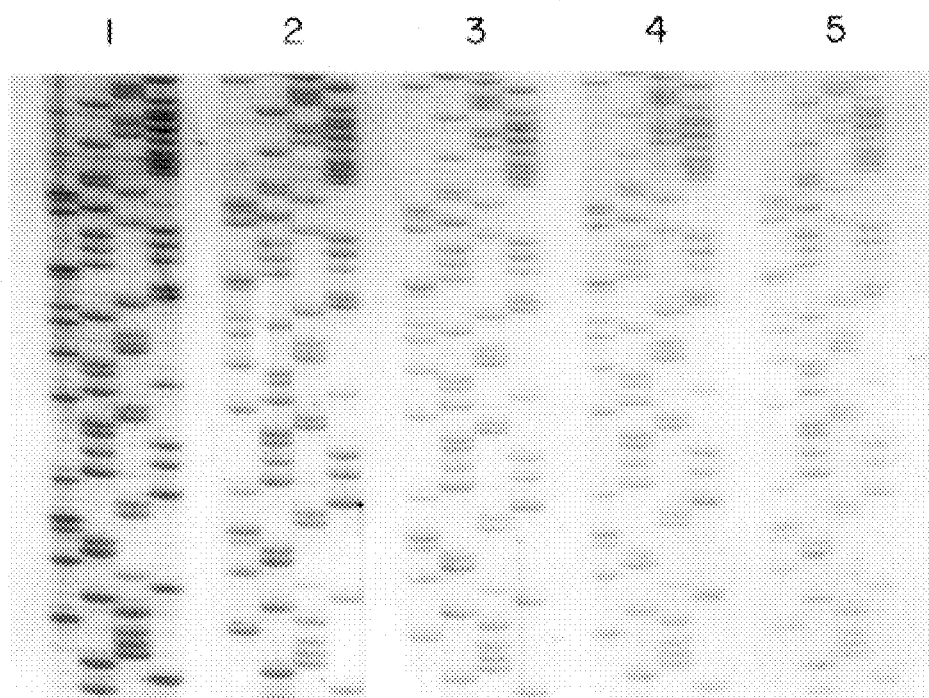

FIGS. 3(A) and 3(B) show the results from silver staining of the DNA sequencing polyacrylamide gel by Bassam et al's method and the invented method after treatment with 0.2% (v/v) polyacrylic acid. In FIGS. 3(A) and 3(B), lanes 1–5 contain 200 ng, 100 ng, 40 ng, 20 ng, and 10 ng of the template DNA, respectively.

As shown in FIGS. 3 (A) and 3 (B), in contrast with the conventional Bassam et al's method which can detect DNA of 100 ng level, the present method accompanying polyacrylic acid treatment can detect DNA even when 10 ng of template DNA was employed. Accordingly, it was clearly determined that the invented silver staining method can also be available for DNA sequencing with a high sensitivity and reproducibility.

As clearly illustrated and demonstrated as above, the present invention provides an improved method for high-sensitive silver staining of DNA molecules with a high sensitivity, which can detect even ng level of DNA molecules. Accordingly, the silver staining method of the invention can be applied for the detection and sequencing of trace amount of DNA.

What is claimed is:

1. A method for high-sensitive silver staining of DNA which comprises the steps of:

linking DNA to a polymer which has a high affinity for DNA, to give a DNA-polymer complex by immersing a DNA containing gel in an aqueous solution containing the polymer; and, binding silver ions to the DNA-polymer complex, to induce silver staining of the DNA.

2. The method for high-sensitive silver staining of claim 1, wherein the polymer is polyacrylic acid or polyethyleneimine.

3. The method for high-sensitive silver staining of claim 1, wherein the solvent employed in the aqueous solution is water.

4. The method for high-sensitive silver staining of claim 1, wherein the concentration of the polymer in the aqueous solution ranges 0.2% (v/v) to 0.4% (v/v).

5. The method for high-sensitive silver staining of claim 1, wherein the DNA containing gel is for DNA sequencing.

6. The method for high-sensitive silver staining of claim 1, wherein the DNA containing gel is for DNA detection.

* * * * *